US012573485B2

(12) United States Patent
    Bender et al.

(10) Patent No.: US 12,573,485 B2
(45) Date of Patent: Mar. 10, 2026

(54) SELECTION OF ANTIBODIES / ANTIBODY FRAGMENTS

(71) Applicant: Bayer Aktiengesellschaft, Leverkusen (DE)

(72) Inventors: Christian Bender, Cologne (DE); Johanna Völker, Berlin (DE)

(73) Assignee: BAYER AKTIENGESELLSCHAFT (DE)

( * ) Notice: Subject to any disclaimer, the term of this patent is extended or adjusted under 35 U.S.C. 154(b) by 545 days.

(21) Appl. No.: 16/929,585

(22) Filed: Jul. 15, 2020

(65) Prior Publication Data

US 2021/0020286 A1 Jan. 21, 2021

(30) Foreign Application Priority Data

Jul. 18, 2019 (EP) ..................................... 19187005

(51) Int. Cl.
    *G16H 20/10*     (2018.01)
    *C12Q 1/6883*     (2018.01)
    *G16H 50/20*     (2018.01)

(52) U.S. Cl.
    CPC ........... *G16H 20/10* (2018.01); *C12Q 1/6883* (2013.01); *G16H 50/20* (2018.01)

(58) Field of Classification Search
    None
    See application file for complete search history.

(56) References Cited

U.S. PATENT DOCUMENTS

2013/0178370 A1    7/2013   Lavinder

FOREIGN PATENT DOCUMENTS

WO     WO-2013078455 A2 *   5/2013   ......... C12Q 1/6874

OTHER PUBLICATIONS

DeKosky, B., Kojima, T., Rodin, A. et al. In-depth determination and analysis of the human paired heavy- and light-chain antibody repertoire. Nat Med 21, 86-91 (2015) (Year: 2015).*
Upadhyay, A.A., Kauffman, R.C., Wolabaugh, A.N. et al. BALDR: a computational pipeline for paired heavy and light chain immunoglobulin reconstruction in single-cell RNA-seq data. Genome Med 10, 20 (2018). (Year: 2018).*
Glenn Deng et al. Enrichment with anti-cytokeratin alone or combined with anti-EpCAM antibodies significantly increases the sensitivity for circulating tumor cell detection in metastatic breast cancer patients. Breast Cancer Research 2008, 10:R69 (Year: 2008).*
Jonathan A. Schumacher et al. Evaluation of Enrichment Techniques for Mass Spectrometry. Journal of Molecular Diagnostics, vol. 9, No. 2, Apr. 2007 (Year: 2007).*

(Continued)

*Primary Examiner* — Karlheinz R. Skowronek
*Assistant Examiner* — Mary C Leverett
(74) *Attorney, Agent, or Firm* — MORRISON & FOERSTER LLP

(57) ABSTRACT

The present invention deals with the selection of antibodies and/or antibody fragments in a selection method. Subjects of the present invention are a method, a system and a computer program product for generating score values for pairs of genes which encode the variable domains of light and heavy chains of antibodies and/or antibody fragments. Antibodies and/or antibody fragments can be selected on the basis of the score values.

11 Claims, 8 Drawing Sheets

(56)     References Cited

OTHER PUBLICATIONS

Chaudhary, N. et al. (Mar. 14, 2018). "Analyzing Immunoglobulin Repertoires," Frontiers in Immunology 9(462): 1-18.

He, L. et al. (Aug. 24, 2017). "Hidden Lineage Complexity of Glycan-Dependent HIV-1 Broadly Neutralizing Antibodies Uncovered by Digital Panning and Native-Like gp140 Trimer," Frontiers in Immunology 8(1025): 1-21.

Kaplinsky, J. et al. (Jun. 9, 2014). "Antibody repertoire deep sequencing reveals antigen-independent selection in maturing B cells," PNAS DOI: 10.1073/pnas.1403278111, E2622-E2629.

DeKosky, B. et al. (Jan. 2015). "In-depth determination and analysis of the human paired heavy- and light-chain antibody repertoire," Nature Medicine, 21(1), 86-93.

Upadhyay, A. et al. (Mar. 20, 2018). "BALDR: a computational pipeline for paired heavy and light chain immunoglobulin reconstruction in single-cell RNA-seq data," Genome Medicine, 10:20, 1-18.

* cited by examiner

SELECTION OF ANTIBODIES / ANTIBODY FRAGMENTS

CROSS-REFERENCE TO RELATED APPLICATIONS

This application claims priority benefit to European Application No. 19187005.4, filed Jul. 18, 2019, the entire contents of which is herein incorporated by reference.

FIELD

The present invention relates generally to the selection of antibodies and/or antibody fragments in a selection method and in particular, generating score values for pairs of genes to select antibodies and/or antibody fragments.

BRIEF DESCRIPTION OF THE DRAWINGS

The present disclosure will now be described, by way of example only, with reference to the accompanying drawings, in which.

DETAILED DESCRIPTION

Figure 1:
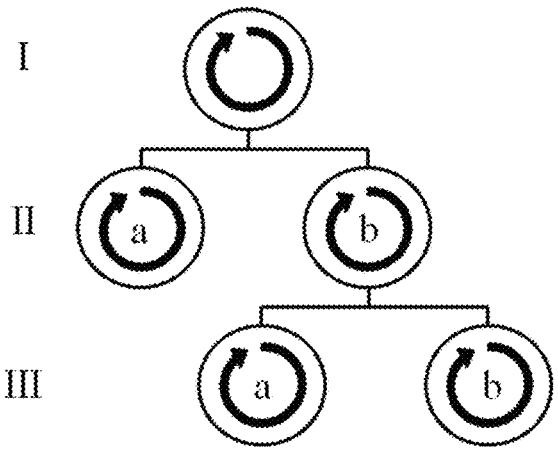
FIG. 1 illustrates a diagram of a selection hierarchy having three levels (I, II, III), according to some embodiments.

Subjects of the present invention are a method, a system and a computer program product for generating score values for pairs of genes which encode the variable domains of light and heavy chains of antibodies and/or antibody fragments. Antibodies and/or antibody fragments can be selected on the basis of the score values.

The human immune system forms a complex network of various organs, cell types and molecules as a defence system against exogenous invaders.

Antibodies, also called immunoglobulins, are proteins from the class of the globulins that are formed in vertebrates as a response to certain substances, what are known as antigens. Antibodies serve the immune system; they are produced by a class of white blood cells, the B lymphocytes.

What act as antigens are almost exclusively macromolecules or particle-bound molecules, for example lipopolysaccharides on the surface of bacteria. A particular antigen generally induces the formation of only a few particular antibodies, which in most cases only recognize, via specific, non-covalent bonds, this foreign substance.

The specific binding of antibodies to antigens forms a major part of the defence against foreign substances which have invaded.

Every antibody consists of two identical heavy chains (H) and two identical light chains (L), which are linked to one another by covalent disulfide bonds to form a Y-shaped structure. The light chains each consist of one variable domain and one constant domain. They are referred to as $V_L$ and $C_L$. The heavy chains by contrast each have one variable domain and three (IgG, IgA) or four (IgM, IgE) constant domains. By analogy, they are referred to as $V_H$ and $C_H1$, $C_H2$, $C_H3$.

The variable domains of one light chain and one heavy chain form the antigen binding site; they are therefore of particular interest for therapeutic, immunological and/or diagnostic purposes. Large libraries of antibodies and/or antibody fragments are created and evaluated for the use thereof in medicine for example.

A widespread technique for generating and characterizing antibody libraries is the "phage display" method, in which the particular protein of interest can be expressed as a fusion polypeptide on a bacteriophage coat protein and selected by binding to immobilized or soluble biotinylated ligands (antigens). A phage constructed in this manner can be regarded as a compact genetic unit which combines both the phenotypic properties and the genotypic properties. "Phage display" technology has been successfully applied to antibodies, antibody fragments, enzymes, DNA-binding proteins, etc.

To use, for example, a phage display of antibody libraries, the relevant cells are first isolated from the organism. These concern plasma cells, which are to be found especially in blood, bone marrow and lymph nodes. From these cells, mRNA is isolated, which is then transcribed into cDNA.

With the aid of the polymerase chain reaction (PCR), the genes of the variable domains of the light chain ($V_L$) and heavy chain ($V_H$) of the antibodies are replicated from the cDNA.

Each set of genes is ligated with the truncated gene of the coat protein pIII (minor coat protein) of the M13 phage in a specific phagemid vector and *Escherichia coli* is transformed therewith.

As a result, the *E. coli* bacteria express pIII fusion proteins containing scFv fragments or Fab antibody fragments. By means of a signal peptide, the fusion proteins are transported into periplasm, where they fold to form a functional scFv or disulfide bond-linked Fab fragment. The Fv or Fab portions initially remain anchored in the inner *E. coli* membrane via the pIII fragment and bind to the capsid when phage assembly is completed.

Via the coat protein pIII, which is normally responsible for bacteria infection, the functional antibody fragment is, after coinfection with an M13 helper phage, incorporated in the outer coat of newly formed phages during the maturation process thereof. At the same time, the phagemid containing the associated genetic information for the corresponding antibody fragment is incorporated in the interior of the newly formed phages. Thus, each of these recombinant phages has theoretically a different antibody fragment on its surface and, at the same time, the associated genes ($V_L$ and $V_H$) in its interior, comparable with the billions of B cells in the (human) body.

In a so-called biopanning procedure, the "binding" phages can be selected from the billion-fold background of irrelevant phages by interaction with fixed ligands (antigens) via the antibody fragments exposed on the surface.

Usually, biopanning involves passing through multiple selection cycles (panning rounds). Usually, this involves exposing a phage display library to a substrate so that the binding of some phages can take place. Non-specifically binding and weakly binding phages are washed off. Phages which are still binding after washing and are hence specific are subsequently detached (eluted). The eluted phages are multiplied and exposed to the substrate again in further panning rounds until there is an enriched population of efficiently binding phages.

At the end of the selection process, the associated antibody genes can be easily isolated and sequenced from the isolated phages. Sequencing then yields information about the blueprints of the antibody (fragments). Further methods for selecting antibodies and/or antibody fragments are described in the literature (see, for example, Sai T. Reddy et al.: *Monoclonal antibodies isolated without screening by analyzing the variable-gene repertoire of plasma cells*, Nature Biotechnology Vol. 28 No. 9, September 2010, 965-971).

A standard method for sequence determination is the Sanger dideoxy method (chain-termination synthesis). The length of the DNA segments sequenced in this way (reads) can reach more than 1000 base pairs, but this is associated with high costs and expenditure of time. An alternative is next-generation sequencing (NGS). Owing to the detection of many parallelly running and spatially separated sequencing reactions on a very small area, a distinctly higher throughput with shorter read lengths is rapidly achieved in comparison with the standard. NGS achieves a magnitude of $10^6$ sequencing reactions. This means that it is possible to determine the diversity and quality of an entire library.

In a biopanning selection method, the last pool still contains a multiplicity of different antibody fragments despite constant enrichment of specifically binding antibody fragments. The number is too large for detailed investigation of all antibody fragments; a selection must be made. In many cases, the antibody fragments are ranked according to the number of their $V_H$ genes in the last pool. The greater the enrichment of the antibody fragments, the higher too, generally, the number of their $V_H$ genes in the last pool.

However, the number of $V_H$ genes in the last pool is not an adequate criterion for the selection of particularly interesting and/or worthwhile antibodies.

It would therefore be desirable to have a better aid available for the identification of promising antibody fragments.

This object is achieved by the subjects of the independent claims. Preferred embodiments are found in the dependent claims, the present description and the drawings.

The present invention provides, in a first aspect, a method comprising the steps of:

receiving features relating to $V_L$ genes and $V_H$ genes, the $V_L$ genes and $V_H$ genes encoding the variable domains of light and heavy chains of antibodies and/or antibody fragments, the antibodies and/or antibody fragments originating from a selection method, the selection method comprising multiple successive selection cycles, the result of each selection cycle being a pool containing antibodies and/or antibody fragments, forming feature vectors for pairs of $V_L$ genes and $V_H$ genes in the pools, the $V_L$ gene and the $V_H$ gene of each pair encoding variable domains belonging to the same antibody and/or antibody fragment, each feature vector for a pool comprising at least the following features:

count of the $V_L$ gene in the particular pool, count of the $V_H$ gene in the particular pool, count of the $V_L$ gene in the preceding pool, count of the $V_H$ gene in the preceding pool, the absolute difference between the count of the $V_H$ gene in the particular pool and the count of the $V_L$ gene in the particular pool, the absolute difference between the count of the $V_H$ gene in the preceding pool and the count of the $V_L$ gene in the preceding pool, identifying enrichment patterns in the feature vectors of the pools, enrichment patterns showing the strength of enrichment of the antibody and/or antibody fragment with the particular $V_L$ gene and $V_H$ gene in the selection method, ascertaining score values for pairs of $V_L$ genes and $V_H$ genes on the basis of the enrichment patterns, the score values correlating with the respective strength of enrichment, optionally: ascertaining a ranking list for pairs of $V_L$ genes and $V_H$ genes on the basis of the score values, outputting the score values and/or the ranking list to a user.

The present invention further provides a system comprising:

an input unit, a feature vector generation unit, an enrichment analysis unit, a score value calculation unit, a ranking unit and an output unit, the input unit being configured to acquire features relating to $V_L$ genes and $V_H$ genes encoding variable domains of light and heavy chains of antibodies and/or antibody fragments, the antibodies and/or antibody fragments originating from a selection method, the selection method comprising multiple successive selection cycles, the result of each selection cycle being a pool containing antibodies and/or antibody fragments, the feature vector generation unit being configured to generate feature vectors for pairs of $V_L$ and $V_H$ genes in the pools on the basis of the acquired features, the $V_L$ gene and the $V_H$ gene of each pair encoding variable domains belonging to the same antibody and/or antibody fragment, each feature vector for a pool comprising at least the following features:

count of the $V_L$ gene in the particular pool, count of the $V_H$ gene in the particular pool, count of the $V_L$ gene in the preceding pool, count of the $V_H$ gene in the preceding pool,

the absolute difference between the count of the $V_H$ gene in the particular pool and the count of the $V_L$ gene in the particular pool, the absolute difference between the count of the $V_H$ gene in the preceding pool and the count of the $V_L$ gene in the preceding pool, the enrichment analysis unit being configured to identify enrichment patterns in the feature vectors of the pools, enrichment patterns showing the strength of enrichment of the antibody and/or antibody fragment with the particular $V_L$ gene and $V_H$ gene in the selection method, the score value calculation unit being configured to calculate score values for pairs of $V_L$ genes and $V_H$ genes on the basis of the enrichment patterns, the score values correlating with the respective strength of enrichment, the ranking unit being preferably configured to calculate a ranking list for pairs of $V_L$ genes and $V_H$ genes on the basis of the score values, the output unit being configured to output the score values and/or the ranking list to a user.

The present invention further provides a computer program product comprising a data carrier, and program code which is stored on the data carrier and which prompts a computer system, in the memory of which the program code is loaded, to execute the following steps:

receiving features relating to $V_L$ genes and $V_H$ genes, the $V_L$ genes and $V_H$ genes encoding the variable domains of light and heavy chains of antibodies and/or antibody fragments, the antibodies and/or antibody fragments originating from a selection method, the selection method comprising multiple successive selection cycles, the result of each selection cycle being a pool containing antibodies and/or antibody fragments, forming feature vectors for pairs of $V_L$ genes and $V_H$ genes in the pools, the $V_L$ gene and the $V_H$ gene of each pair encoding variable domains belonging to the same antibody and/or antibody fragment, each feature vector for a pool comprising at least the following features:

count of the $V_L$ gene in the particular pool,
count of the $V_H$ gene in the particular pool,
count of the $V_L$ gene in the preceding pool,
count of the $V_H$ gene in the preceding pool,
the absolute difference between the count of the $V_H$ gene in the particular pool and the count of the $V_L$ gene in the particular pool,
the absolute difference between the count of the $V_H$ gene in the preceding pool and the count of the $V_L$ gene in the preceding pool, identifying enrichment patterns in the feature vectors of the pools, enrichment patterns showing the strength of enrichment of the antibody and/or antibody fragment with the particular $V_L$ gene and $V_H$ gene in the selection method, ascertaining score values for pairs of $V_L$ genes and $V_H$ genes on the basis of the enrichment patterns, the score values correlating with the respective strength of enrichment, optionally: ascertaining a ranking list for pairs of $V_L$ genes and $V_H$ genes on the basis of the score values, outputting the score values and/or the ranking list to a user.

The invention will be more particularly elucidated below without distinguishing between the subjects of the invention. On the contrary, the following elucidations are intended to apply analogously to all the subjects of the invention, irrespective of in which context they occur.

If steps are stated in an order in the present description or in the claims, this does not necessarily mean that the invention is restricted to the stated order. On the contrary, it is conceivable that the steps can also be executed in a different order or else in parallel to one another, unless one step builds upon another step, this absolutely requiring that the building step be executed subsequently (this being, however, clear in the individual case). The stated orders are thus preferred embodiments.

One starting point for the present invention is a library of antibodies and/or antibody fragments. Said antibodies and/or antibody fragments are introduced to a selection method in order to select antibodies and/or antibody fragments on the basis of their phenotypic properties. The selection method can, for example, be a biopanning method.

A selection method in the context of the present invention comprises multiple successive selection cycles. The result of each selection cycle is a pool containing antibodies and/or antibody fragments. The goal of the selection method is an enrichment of specifically binding antibodies and/or antibody fragments. This means that any selection cycle pool has a higher concentration of specifically binding antibodies and/or antibody fragments than a pool preceding said pool.

FIG. 1 shows an example of a selection hierarchy having three levels (I, II, III). In the first level (I), a library of antibodies and/or antibody fragments is introduced to a first selection cycle. The result of the first selection cycle is a pool of selected antibodies and/or antibody fragments. In the second level (II), the selected antibodies and/or antibody fragments are introduced to two selection cycles (a and b). Generally, the selection cycles in the second level are different selection cycles. The results of the selections in the second level are, in turn, two pools of selected antibodies and/or antibody fragments. In the third level (III), the pool of antibodies and/or antibody fragments that results from the right branch (IIb) of the second level is again exposed to two selection cycles (a and b), which, in turn, result in two pools. Generally, the antibodies and/or antibody fragments are exposed to an increasing selection pressure when passing through a selection hierarchy from top to bottom (e.g. from the first level to the third level via the second level). When passing through a selection hierarchy from top to bottom (I→IIb→IIIb), the diversity of the antibodies and/or antibody fragments in the respective pools decreases.

It is conceivable that different targets are used in the selection cycles. For example, when searching for therapeutically effective antibodies or when searching for antibodies for diagnostic purposes, it is customary to investigate the binding of the antibodies not only in relation to a human target, but also in relation to a murine target. Accordingly, a selection method often has at least two branches, the antibodies in one branch being exposed to an increasing selection pressure with respect to a first target (e.g. a mouse target) and the antibodies in the second branch being exposed to an increasing selection pressure with respect to a second target (e.g. a human target) (e.g. see: WO0220822A2).

Preferably, the selection method comprises at least two, preferably at least 3, yet more preferably at least 4, most preferably at least 5 selection levels.

Following a selection cycle, genes of the selected antibodies and/or antibody fragments are usually sequenced in order to identify them.

Sequencing involves determining the $V_L$ genes encoding the variable domains of light chains of the antibodies and/or antibody fragments and the $V_H$ genes encoding the variable domains of the heavy chains of the antibodies and/or antibody fragments. At the same time, their counts in the respective pool are determined.

It is conceivable that such a sequencing step is carried out after each selection cycle. It is also conceivable that such a sequencing step is only carried out after passing through a hierarchy of multiple cycles. It is conceivable that a certain enrichment of specifically binding antibodies and/or antibody fragments is to be achieved first before a characterization by sequencing takes place.

In a further step, features relating to the $V_L$ and $V_H$ genes in the respective pools are acquired/ascertained and feature vectors for pairs of $V_L$ genes and $V_H$ genes are generated, the $V_L$ gene and the $V_H$ gene of each pair encoding variable domains belonging to the same antibody and/or antibody fragment.

Generally, a feature vector combines the (preferably numerically) parameterizable properties (features) of an object in a vectorial manner. Various features characteristic of the object form the various dimensions of said vector. The entirety of possible feature vectors is called the feature space. Feature vectors facilitate, for example, an automatic classification, since they greatly reduce the properties to be classified.

In the present case, the object is a pair of a $V_L$ gene and a $V_H$ gene in a pool, the $V_L$ gene and the $V_H$ gene encoding variable domains belonging to the same antibody and/or antibody fragment.

One way of identifying pairs of $V_L$ genes and $V_H$ genes, in which the $V_L$ gene and the $V_H$ gene encode variable domains belonging to the same antibody and/or antibody fragment, is described in the international patent application with the publication number WO2019206729, the entire content of which is incorporated in this description by reference. Since said patent application was not yet disclosed on the priority date of the present property right, the essential aspects in relation to identifying pairs of $V_L$ genes and $V_H$ genes, in which the $V_L$ gene and the $V_H$ gene encode variable domains belonging to the same antibody and/or antibody fragment, are presented in the last section of the present description.

A feature vector characterizes a pair of a $V_L$ gene and a $V_H$ gene in a pool. For the same pair in another pool (e.g. the preceding pool), a separate feature vector is generated. Similarly, for another pair in the same pool, a separate feature vector is also generated. According to the invention, what go into a feature vector for a pair in a pool are not only items of information about the pair in the pool, but also, for example, items of information about the same pair in the preceding pool.

A feature vector for a pair of a $V_L$ gene and a $V_H$ gene for a pool comprises at least the following features:

count of the $V_L$ gene in the particular pool (preferably in the form of the absolute number VL of $V_L$ genes in the pool or in normalized form), count of the VH gene in the particular pool (preferably in the form of the absolute number VH of $V_H$ genes in the pool or in normalized form), count of the $V_L$ gene in the preceding pool (preferably in the form of the absolute number prevVL of the $V_L$ gene in the preceding pool or in normalized form)

count of the $V_H$ gene in the preceding pool (preferably in the form of the absolute number prevVH of the $V_H$ gene in the preceding pool or in normalized form)

the absolute difference (diff) between the count of the $V_H$ gene in the particular pool and the count of the $V_L$ gene in the particular pool (diff=|VH-VL|)

the absolute difference (prevDiff) between the count of the $V_H$ gene in the preceding pool and the count of the $V_L$ gene in the preceding pool (prevDiff=|prevVH-prevVL|).

Important features relating to $V_L$ and $V_H$ genes in a pool are the counts with which they occur in the particular pool (preferably in the form of the absolute numbers VH and VL or in normalized form). The counts are preferably acquired by next-generation sequencing methods, by assembling the fragmented genetic information of $V_H$ and $V_L$ sequences to form complete $V_H$ and $V_L$ chains (or parts thereof) with the aid of paired recognition sequences (primer pairs). The unambiguous sequences are then counted and outputted in the form of DNA counts.

The normalization of counts can, for example, be done on the basis of the following formulae:

$$\text{rpm}VH=(VH/\text{sum}VH)*1000000$$

$$\text{rpm}VL=(VL/\text{sum}VL)*1000000$$

where rpmVH is the normalized count of the $V_H$ genes in the observed pool, where rpmVL is the normalized count of the $V_L$ genes in the observed pool, where sumVH is the sum of the absolute counts VH of all $V_H$ genes in the observed pool, where sumVL is the sum of the absolute counts VL of all $V_L$ genes in the observed pool.

Further important features are the count of the $V_L$ gene in the preceding pool and the count of the $V_H$ gene in the preceding pool. The preceding pool is preferably understood to mean that pool which is one level above in the selection hierarchy, i.e. immediately before an observed pool in the order of the selection cycles which are passed through. The antibodies/antibody fragments isolated from the preceding pool are introduced to the selection cycle having the observed pool as its result. The count of the $V_L$ genes and the $V_H$ genes in the preceding pool can, too, be used in the form of absolute counts or in normalized form in a feature vector.

Further important features are the absolute difference (diff) between the count of the $V_H$ gene in the observed pool and the count of the $V_L$ gene in the observed pool (diff=|VH-VL|) and also the absolute difference (prevDiff) between the count of the $V_H$ gene in the preceding pool and the count of the $V_L$ gene in the preceding pool (prevDiff=|prevVH-prevVL|).

Furthermore, further features can be incorporated in the feature vector, such as, for example:

the absolute number (count) of different $V_H$ genes in the observed pool: numVH the absolute number (count) of different $V_L$ genes in the observed pool: numVL the absolute number (count) of that $V_H$ gene which is present in the observed pool with the greatest count: maxVH the absolute number (count) of that $V_L$ gene which is present in the observed pool with the greatest count: maxVL the relative count of the $V_H$ gene in the observed pool (based on the number of the $V_H$ gene which occurs in the observed pool with the greatest count): relVH=VH/maxVH the relative count of the $V_L$ gene in the observed pool (based on the number of the $V_L$ gene which occurs in the observed pool with the greatest count): relVL=VL/maxVL the relative difference (relative distance) between the count of the $V_H$ gene in the observed pool and the count of the $V_L$ gene in the observed pool (in relation to the count of that gene in the observed pool which occurs with a greater count): reldiff=|VH−VL|/max(VH, VL), where max(VH, VL)=H for VH>VL and max(VH, VL)=VL for VL≥VH the number of selection cycles (levels) which were passed through before the observed selection cycle: prevnum normalized count of the $V_H$ genes in the observed pool: rpmVH=(VH/sumVH)*1000000, where sumVH is the sum of the counts VH of all $V_H$ genes in the observed pool normalized count of the $V_L$ genes in the observed pool: rpmVL=(VL/sumVL)*1000000, where sumVL is the sum of the counts VL of all $V_L$ genes in the observed pool normalized count of the $V_H$ genes in the preceding pool: prevRpmVH=(prevVH/prevSumVH)*1000000, where prevSumVH is the sum of the counts VH of all $V_H$ genes in the preceding pool normalized count of the $V_L$ genes in the preceding pool: prevRpmVL=(prevVL/prevSumVL)*1000000, where prevSumVL is the sum of the counts VL of all $V_L$ genes in the preceding pool the relative change in the number of $V_H$ genes from the first selection cycle to the second selection cycle: prevRelDiffV$_H$=(|VH−prevVH|)/max(VH, prevVH), where max(VH, prevVH)=VH for VH>prevVH and max(VH, prevVH)=prevVH for prevVH≥VH the relative change in the number of $V_L$ genes from the first selection cycle to the second selection cycle: prevRelDiffV$_L$=(|VL−prevVL|)/max(VL, prevVL), where max(VL, prevVL)=VL for VL>prevVL and max (VL, prevVL)=prevVL for prevVL≥VL the logarithm to the base 2 of the ratio of the normalized count of the $V_H$ genes in the observed pool to the normalized count of the $V_H$ genes in the preceding pool: logRpmVH=log 2(rpmVH/prevRpmsVH)

the logarithm to the base 2 of the ratio of the normalized count of the $V_L$ genes in the observed pool to the normalized count of the $V_L$ genes in the preceding pool: logRpmVL=log 2(rpmVL/prevRpmsVL)

It is conceivable that further items of information besides the stated features are acquired/ascertained and go into the generation of feature vectors. For example, counts of $V_H$ genes and $V_L$ genes in pools from further selection cycles can be acquired as features and go into the generation of feature vectors. Furthermore, features relating to selection hierarchy and/or parameters of the individual selection cycles can also be acquired and go into the generation of feature vectors. For example, these include also items of information about the substrates used in the selection cycles, parameters relating to carrying out the sequencing cycles (concentrations, temperatures, media, and others), structure of the sequencing hierarchy (number of levels and/or branches), and others.

The feature vector usually comprises an unambiguous identifier for the particular $V_L$ gene and an unambiguous identifier for the particular $V_H$ gene. The unambiguous identifiers serve to identify the observed $V_H$ gene and observed $V_L$ gene. An unambiguous identifier can, for example, be a gene sequence, a name, a code number, an alphanumerical identification code or some other identifier, by means of which a $V_L$ gene or a $V_H$ gene is unambiguously designated and hence made identifiable. The unambiguous identifiers are therefore primarily used for processing the results and for assigning the results to the corresponding $V_H$ and $V_L$ genes. It is also conceivable that the $V_L$ gene belonging to a pair and the $V_H$ gene belonging to the pair are not each individually provided with an unambiguous identifier and that instead the pair is characterized by an unambiguous identifier.

An example of a preferred feature vector for a pair of a $V_L$ gene and a $V_H$ gene having the respective identifiers x and y is:

<x, y, VL, VH, diff, relDiff, prevVL, prevVH, prevDiff>

An example of a particularly preferred feature vector for a pair of a $V_L$ gene and a $V_H$ gene having the respective identifiers x and y is:

<x, y, rpmVL, rpmVH, diff, relDiff, prevDiff, prevRpmVH, prevRpmVL, prevNum, logRpmVH, logRpmVL>

The orders in which the features occur in the feature vectors described here can of course also be different to the orders presented here.

In a next step, enrichment patterns are identified in the quantity of data which are formed by the feature vectors. Thus, contrary to what is customary in the prior art, the enrichment of an antibody or an antibody fragment is determined not only on the basis of the counts of genes in the last pool, but also on the basis of features from the last pool and at least one preceding pool. Preferably, feature vectors from at least three, yet more preferably from at least four successive pools are used in order to identify count patterns.

Enrichment patterns are identified in each case for pairs of $V_L$ genes and $V_H$ genes, the $V_L$ gene and the $V_H$ gene of each pair encoding variable domains belonging to the same antibody and/or antibody fragment. The enrichment patterns show the strength of enrichment of the antibody and/or the antibody fragment with the particular $V_L$ gene and $V_H$ gene in the selection method (along the selection cycles from pool to pool). The enrichment patterns thus indicate the binding strengths of the respective antibodies/antibody fragments in relation to the antigen used in the selection method (or the multiple antigens used in the selection method): the stronger the enrichment, the greater the binding strength.

Preferably, enrichment patterns for pairs of $V_L$ genes and $V_H$ genes are identified with respect to multiple different targets, preferably with respect to one or more murine targets and one or more human targets.

For each pair of a $V_L$ gene and a $V_H$ gene, what is subsequently calculated on the basis of the enrichment pattern is, in each case, a score value which quantitatively reflects the enrichment of the corresponding antibody/antibody fragment. Preferably, separate score values for the enrichment with respect to different targets are calculated (e.g. a score value for the enrichment with respect to a murine target and a score value for the enrichment with respect to a human target).

One approach for identifying an enrichment pattern is following the counts of the $V_L$ genes and $V_H$ genes from one pool of the selection method to a next pool. However, according to the invention, what are observed are not only the counts of the $V_L$ genes and $V_H$ genes alone, but also additionally one or more of the above-mentioned further features. Moreover, what are observed are not only the last pool, but also at least two, preferably at least three, yet more preferably at least four successive pools.

For the identification of enrichment patterns, preference is given to using multivariate data analysis methods.

Preferably, a dimension reduction is performed to this end in a first step. Preferably, factors for the pairs of $V_L$ genes and $V_H$ genes in a pool are ascertained on the basis of the feature vectors, which factors describe the properties of the pairs in the pool with a lower number of variables than the feature vectors. A common method is, for example, a principal component analysis (PCA). However, another multivariate data analysis method is also conceivable.

In principal component analysis, a multiplicity of variables are approximated by a lower number of linear combinations that are as informative as possible (the "principal components"). The goal of principal component analysis is to project the data points in a p-dimensional space into a q-dimensional subspace such that, while doing so, as little information as possible is lost and present redundancy is combined in the form of correlation in the data points. In this connection, the positive integers p and q specify the dimensions of the respective spaces. Mathematically, a principal axis transformation is carried out: the correlation of multidimensional features is minimized by transfer into a vector space with a new basis. The principal axis transformation can be specified by an orthogonal matrix which is formed from the eigenvectors of the covariance matrix. Details can be gathered from the extensive technical literature concerning this topic (see, for example, H.-F. Eckey et al.: *Multivariate Statistik*, Gabler Verlag 2002, ISBN-13: 978-3-409-11969-6).

Preferably, the variables of the feature vectors are approximated by a number of factors which encompass at least 70% of the variability of the original data.

In a preferred embodiment, 5 to 7 variables of a feature vector are approximated by 2 or 3 factors (e.g. principal components).

On the basis of the factors, score values for pairs of $V_L$ genes and $V_H$ genes can be generated in a next step. The score values are preferably generated across all pools (having a specific target, for example a murine target or a human target) for which there are feature vectors for the respective pairs. This is (per target) at least two, preferably at least 3, yet more preferably at least 4 feature vectors for each pair.

The score values correlate with the enrichment of the $V_L$ genes and $V_H$ genes (or the corresponding antibodies/antibody fragments) as a consequence of the selection method. Usually, the greater the score value, the more pronounced the enrichment (positive correlation).

The score value reflects the development of the factors for a pair of a $V_L$ gene and a $V_H$ gene from the first (observed) pool to the last (observed) pool of the selection method.

In a preferred embodiment, what is calculated is the sum of those vectors which arise when proceeding along the coordinates of the factors (principal components) of a pool from the first pool up to the last pool. A vector arises for each step from the coordinates of the factors of one pool to the coordinates of the factors of the next pool. The sum of all vectors is a sum vector which, starting from the zero point of the coordinate system, specifies a point in the coordinate system of the factors. The length of said vector can, for example, be specified as a score value. Similarly, it is conceivable that the score value is calculated by multiplication of the coordinates of that point in the coordinate system of the factors that is specified by the sum vector. It is conceivable that the coordinates are weighted before multiplication. It is, for example, conceivable that a higher weight is to be given to the first factor (the first principal component) than, for example, to the second factor (the second principal component). Accordingly, the coordinates for the first factor can be multiplied with a higher weight than the coordinates of the second factor. In a preferred embodiment, the coordinates of the individual factors are weighted equally.

In a next step, the score values can be arranged in a ranking list. To this end, the score values are usually sorted according to their size, for example from the largest score value up to the smallest score value or vice versa. If the score value correlates positively with the enrichment, the large score values indicate the $V_H$-$V_L$ pairs of those antibodies/antibody fragments which have a particularly pronounced specific enrichment. Said antibodies/antibody fragments are therefore of particular interest for therapeutic, immunological and/or diagnostic purposes. The ranking list is, for example, outputted to a user by means of a screen.

As already described, different score values for antibodies and/or antibody fragments can be ascertained, for example a score value for the enrichment with respect to a murine target and a score value for the enrichment with respect to a human target. A ranking list can be generated for each of the different score values.

The calculated score values and/or ranking lists can, for example, be outputted to a user by means of a screen.

The steps of the method according to the invention can be executed with the aid of a computer system or multiple computer systems.

A "computer system" is a system for electronic data processing that processes data by means of programmable calculation rules. Such a system usually comprises a "computer", that unit which comprises a processor for carrying out logical operations, and also peripherals.

In computer technology, "peripherals" refer to all devices which are connected to the computer and serve for the control of the computer and/or as input and output devices. Examples thereof are monitors (screen), printers, scanners, mice, keyboards, drives, cameras, microphones, loudspeakers, etc. Internal ports and expansion cards are also considered to be peripherals in computer technology.

Computer systems of today are frequently divided into desktop PCs, portable PCs, laptops, notebooks, netbooks and tablet PCs and so-called handhelds (e.g. smartphone); all these devices can be utilized for carrying out the invention.

Inputs into the computer are achieved via input means such as, for example, a keyboard, a mouse, a microphone, a network connection, an external data memory and/or the like. Outputs are usually achieved via a screen (monitor), on a printer, via loudspeakers and/or by storage on a data memory.

A system for carrying out the present invention is configured to execute a series of operations. In the present description, the operations have been assigned to specific units: input unit, feature vector generation unit, enrichment analysis unit, score value calculation unit, ranking unit and output unit. However, it is conceivable that the operations are executed by a (single) central processing unit (CPU) of a computer system. Furthermore, it is conceivable that the operations are distributed on various computers (computer systems), it being possible for one computer (computer system) to execute one or more operations of the stated units.

The invention is more particularly elucidated below with reference to figures, without wishing to restrict the invention to the features and combinations of features that are shown in the figures.

The following are shown:

FIG. 1 shows an example of a selection hierarchy having three levels (I, II, III). FIG. 1 is described in detail further above.

Figure 2:
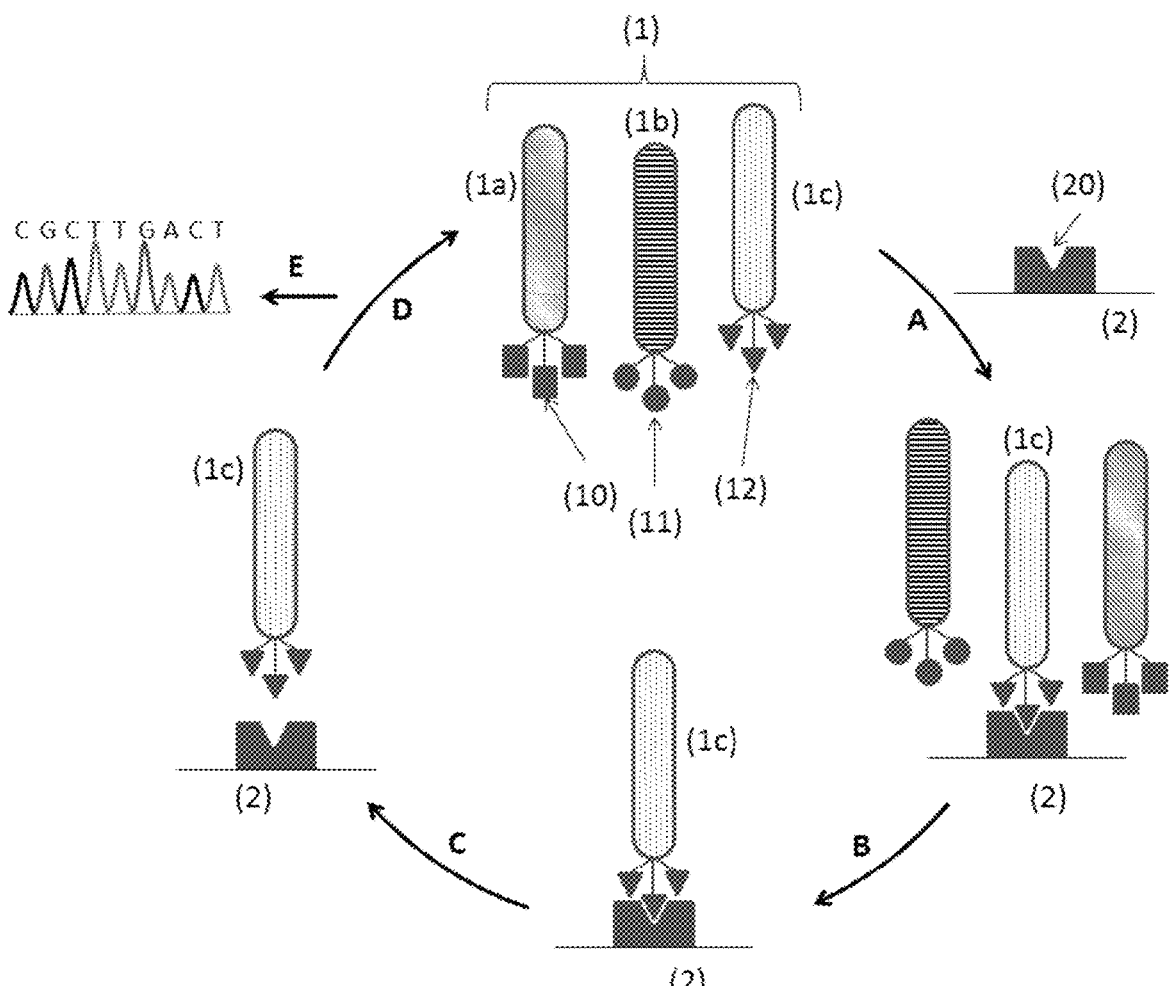
FIG. 2 illustrates a diagram of a biopanning cycle as an example of a selection cycle, according to some embodiments.

FIG. 2 shows schematically a biopanning cycle as an example of a selection cycle.

In a first step, a library (1) of phages (1a, 1b, 1c) in which antibodies and/or antibody fragments (10, 11, 12) are expressed as fusion polypeptides on phage coat proteins is provided.

In addition, a substrate (2) having immobilized antigens and/or antigen fragments is provided. The immobilized antigens and/or antigen fragments have binding sites (20) to which the antibodies and/or antibody fragments (10, 11, 12) of the phages (1a, 1b, 1c) can bind. The antigens/antigen fragments can be antigens/antigen fragments from mouse and/or human.

In step A of the biopanning cycle, the phages are incubated with the substrate.

In the course of this, interactions occur between the antibodies/antibody fragments and the antigens. In the present case, the antibody/antibody fragment (1c) exactly fits the binding site (20) of the immobilized antigen; the interaction and the resulting binding are comparatively strong (stronger than in the case of the other antibodies/antibody fragments).

In step B of the biopanning cycle, the phages which do not bind to the substrate or only bind weakly thereto are separated (washed off). What remain are the more strongly binding phages.

In step C of the biopanning cycle, the more strongly binding phages are detached from the substrate.

In step D of the biopanning cycle, the phages detached from the substrate are multiplied. The result is a new phage library which can be exposed again to a substrate.

From a portion of the phages detached from the substrate, the genes of the antibodies and/or antibody fragments can be sequenced (step E). This involves ascertaining the $V_L$ genes encoding the variable domains of light chains of the antibodies and/or antibody fragments and the $V_H$ genes encoding the variable domains of the heavy chains of the antibodies and/or antibody fragments and also their counts.

Figure 3:
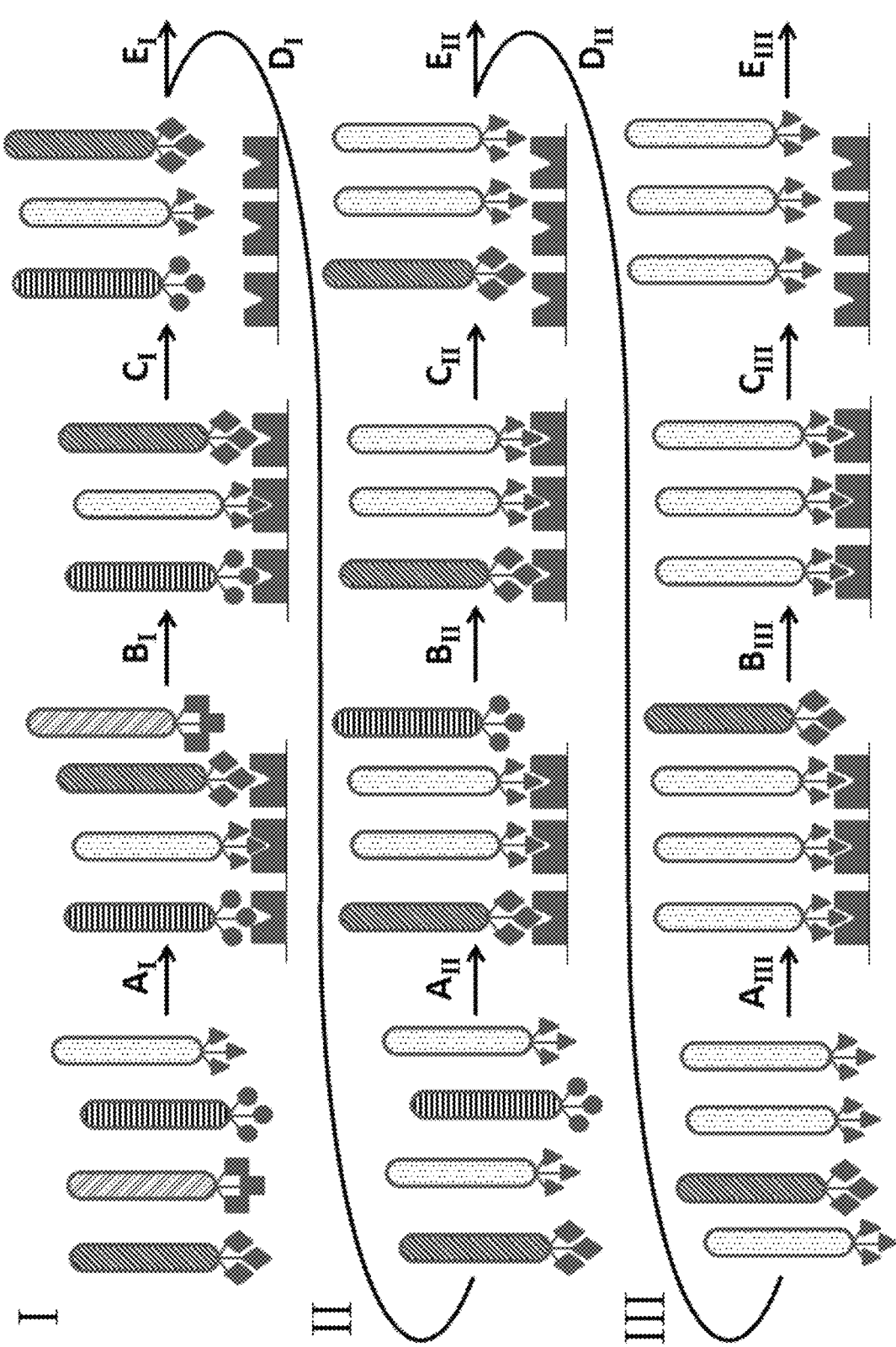
FIG. 3 illustrates a diagram of a biopanning procedure with three cycles (I, II, III), according to some embodiments.

FIG. 3 shows schematically a biopanning procedure with three cycles (I, II, III). As in the present case, if the same substrate is used each time, the strongest binding antibodies/antibody fragments are further enriched with each cycle. Steps $A_I$, $B_I$, $C_I$, $D_I$, $E_I$ or $A_{II}$, $B_{II}$, $C_{II}$, $D_{II}$, $E_{II}$ or $A_{III}$, $B_{III}$, $C_{III}$, $D_{III}$, $E_{III}$ correspond to steps A, B, C, D, E in FIG. 2.

After each cycle (I, II, III), the $V_H$ and $V_L$ genes and their counts can be ascertained (steps $E_1$, $E_{II}$ and $E_{III}$).

Figure 4:
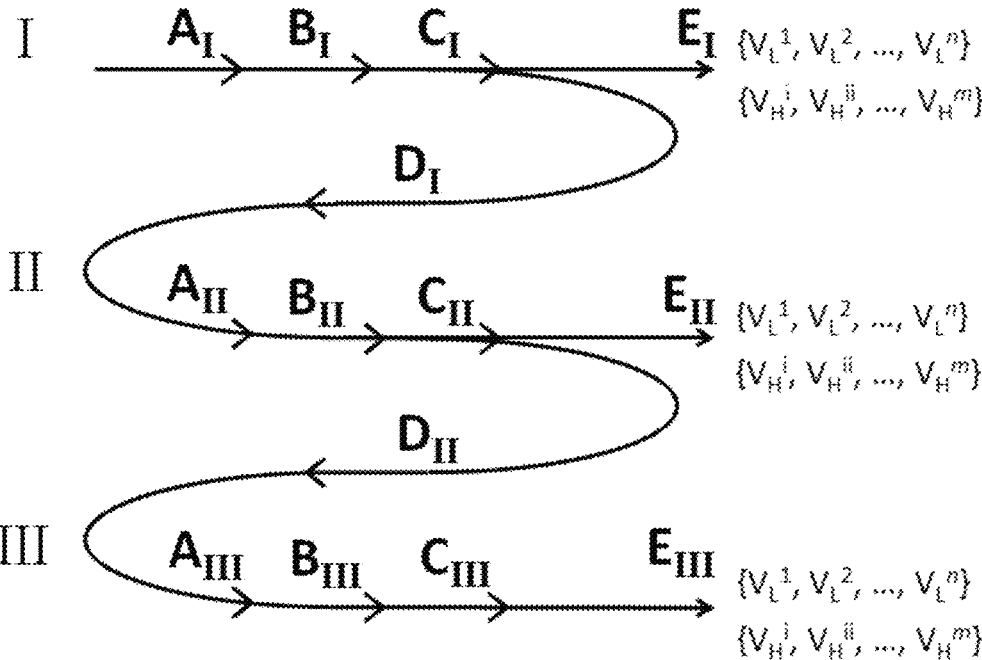
FIG. 4 illustrates a diagram of the same biopanning method as in FIG. 3 with cycles I, II and III including multiple steps, according to some embodiments.

FIG. 4 shows schematically the same biopanning method as in FIG. 3 with cycles I, II and III and steps $A_I$, $A_{II}$, $A_{III}$, $B_I$, $B_{II}$, $B_{III}$, $C_I$, $C_{II}$, $C_{III}$, $D_I$, $D_{II}$, $D_{III}$, $E_I$, $E_{II}$ and $E_{III}$. The result of steps $E_I$, $E_{II}$ and $E_{III}$ is, in each case, a pool of $V_L$ genes $\{V_L^1, V_L^2, \ldots, V_L^n\}$ and a pool of $V_H$ genes $\{V_H^i, V_H^{ii}, \ldots, V_H^m\}$; each gene is identifiable on the basis of an unambiguous identifier (1, 2, . . . to n or i, ii, . . . to m).

Figures 5, 6:
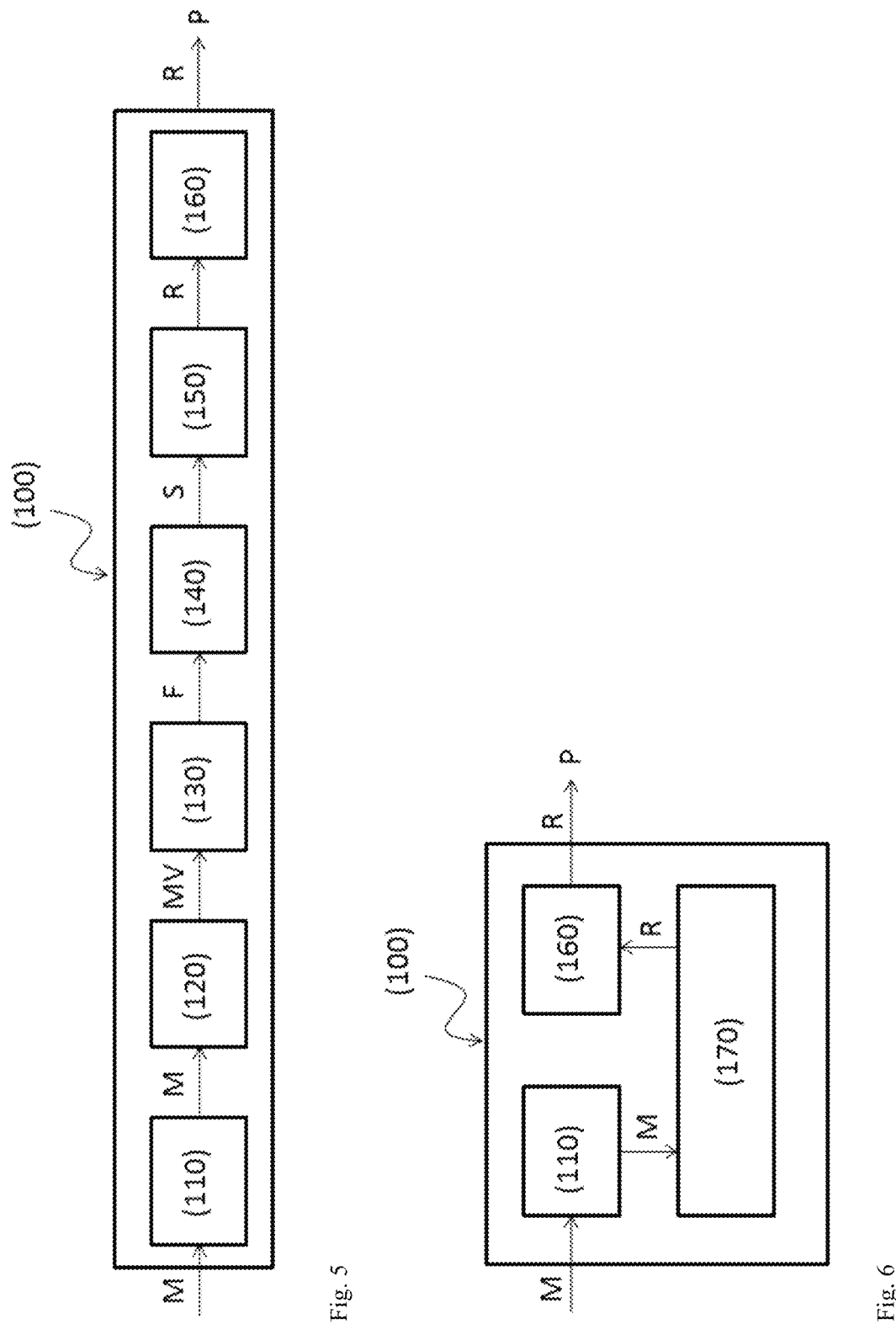
FIG. 5 illustrates a block diagram of a system for selecting antibodies and/or antibody fragments, according to some embodiments.
FIG. 6 illustrates a block diagram of a system for selecting antibodies and/or antibody fragments, according to some embodiments.

FIG. 5 shows schematically one embodiment of the system according to the invention. The system (100) comprises an input unit (110), a feature vector generation unit (120), an enrichment analysis unit (130), a score value calculation unit (140), a ranking unit (150) and an output unit (160).

Via the input unit (110), features M relating to $V_L$ genes and $V_H$ genes encoding variable domains of light and heavy chains of antibodies and/or antibody fragments from a selection method enter the system (100). The features M are transmitted to the feature vector generation unit (120). On the basis of the features M, the feature vector generation unit (120) generates feature vectors MV for pairs of $V_L$ and $V_H$ genes in the respective pools of the selection method, the $V_L$ gene and the $V_H$ gene of each pair encoding variable domains belonging to the same antibody and/or antibody fragment. The feature vectors MV are transmitted to the enrichment analysis unit (130). On the basis of the feature vectors MV, the enrichment analysis unit (130) generates factors F which describe the properties of the $V_L$-$V_H$ pair in a pool with a lower number of variables than the feature vectors. The factors F are transmitted to the score value calculation unit (140). On the basis of the factors F, the score value calculation unit (140) calculates score values S for $V_L$-$V_H$ pairs. The score values S are transmitted to the ranking unit (150). On the basis of the score values S, the ranking unit (150) generates a ranking list R for $V_L$-$V_H$ pairs. The ranking list R is transmitted to the output unit (160). The output unit (160) outputs the ranking list R to a user P.

The system (100) according to the invention can, for example, be configured as a computer system (e.g. desktop computer, tablet computer, smartphone, server) or a combination of computer systems.

FIG. 6 shows schematically a further embodiment of the system according to the invention. The system (100) comprises an input unit (110), a control and calculation unit (170) and an output unit (160).

The control and calculation unit (170) is configured:

to prompt the input unit (110) to receive features M relating to $V_L$ genes and $V_H$ genes, the $V_L$ genes and $V_H$ genes encoding the variable domains of light and heavy chains of antibodies and/or antibody fragments, the antibodies and/or antibody fragments originating from a selection method, the selection method comprising multiple successive selection cycles, the result of each selection cycle being a pool containing antibodies and/or antibody fragments, to generate feature vectors for pairs of $V_L$ genes and $V_H$ genes in the pools, the $V_L$ gene and the $V_H$ gene of each pair encoding variable domains belonging to the same antibody and/or antibody fragment, to generate factors for the pairs of $V_L$ genes and $V_H$ genes in a pool on the basis of the feature vectors, the factors describing the properties of the pairs in a pool with a lower number of variables than the feature vectors, to calculate score values for pairs of $V_L$ genes and $V_H$ genes on the basis of the factors, to generate a ranking list R for pairs of $V_L$ genes and $V_H$ genes on the basis of the score values, to prompt the output unit (160) to output the ranking list R to a user P.

The system (100) according to the invention can, for example, be configured as a computer system (e.g. desktop computer, tablet computer, smartphone, server) or a combination of computer systems.

Figure 7:
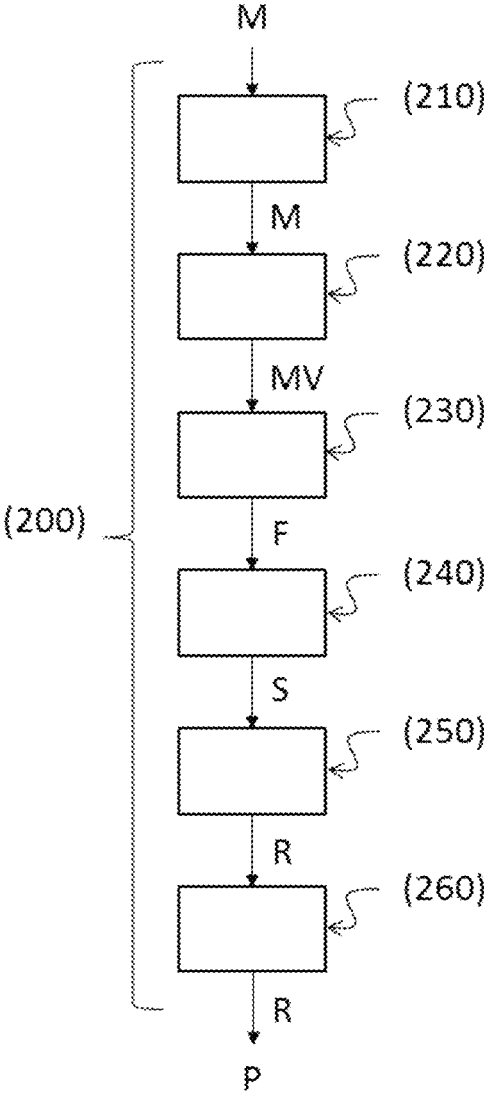
FIG. 7 illustrates a flow chart of a method for selecting antibodies and/or antibody fragments, according to some embodiments.

FIG. 7 shows a preferred embodiment of the method according to the invention in the form of a flow chart. The method (200) comprises the steps:

(210) receiving features M relating to $V_L$ genes and $V_H$ genes, the $V_L$ genes and $V_H$ genes encoding the variable domains of light and heavy chains of antibodies and/or antibody fragments, the antibodies and/or antibody fragments originating from a selection method, the selection method comprising multiple successive selection cycles, the result of each selection cycle being a pool containing antibodies and/or antibody fragments, (220) forming feature vectors MV for pairs of $V_L$ genes and $V_H$ genes in the pools on the basis of the features M, the $V_L$ gene and the $V_H$ gene of each pair encoding variable domains belonging to the same antibody and/or antibody fragment, each feature vector for a pool comprising at least the following features:

count of the $V_L$ gene in the particular pool,
count of the $V_H$ gene in the particular pool, count of the $V_L$ gene in the preceding pool, count of the $V_H$ gene in the preceding pool, the absolute difference between the count of the $V_H$ gene in the particular pool and the count of the $V_L$ gene in the particular pool, the absolute difference between the count of the $V_H$ gene in the preceding pool and the count of the $V_L$ gene in the preceding pool, (230) ascertaining factors F for the pairs of $V_L$ genes and $V_H$ genes in a pool on the basis of the feature vectors MV, the factors F describing the properties of the pairs in a pool with a lower number of variables than the feature vectors, (240) ascertaining score values S for pairs of $V_L$ genes and $V_H$ genes on the basis of the factors F, (250) ascertaining a ranking list R for pairs of $V_L$ genes and $V_H$ genes on the basis of the score values S, (260) outputting the ranking list R to a user P.

Figure 8:
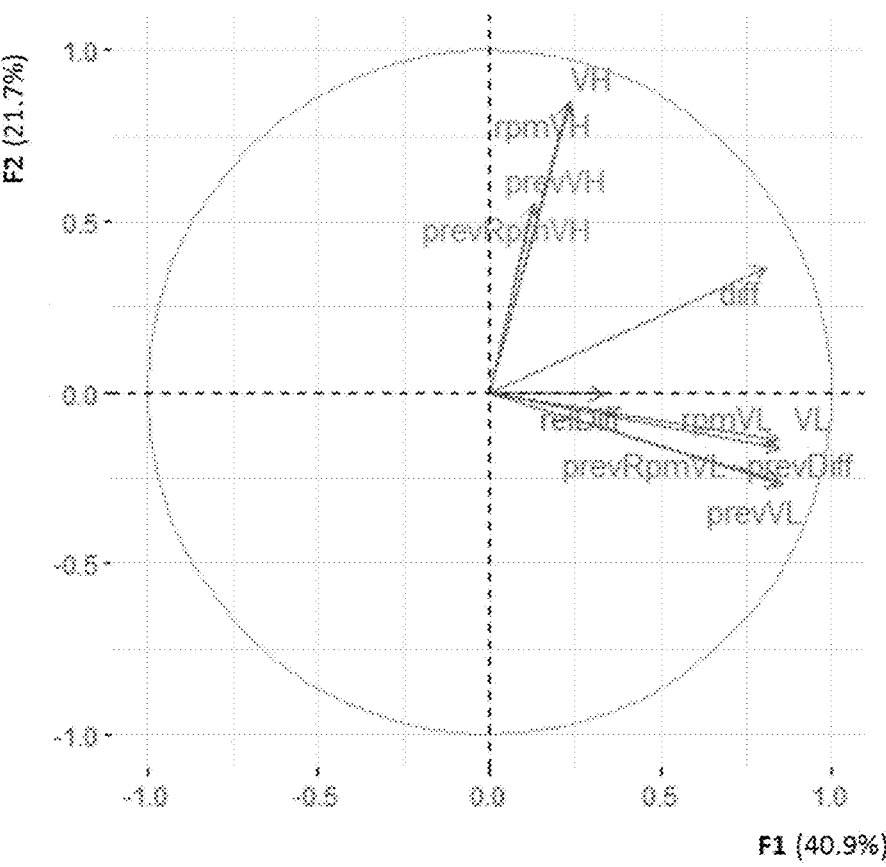
FIG. 8 illustrates a graph showing a result of a principal component analysis of feature, according to some embodiments.

FIG. 8 shows, by way of example, the result of a principal component analysis of feature vectors in the form of a graph. Here, F1 is the first principal component and F2 is the second principal component. The graph shows the proportion of the principal components F1 and F2 due to the variables of the feature vectors. For example, it is evident that the number VH of $V_H$ genes has a large proportion of the principal component F2, whereas the number VL of VL genes has a large proportion of the principal component F1. 40.9% of the variability of the data can be explained by means of the principal component F1, and 21.7% of the data by means of principal component F2.

Figure 9:
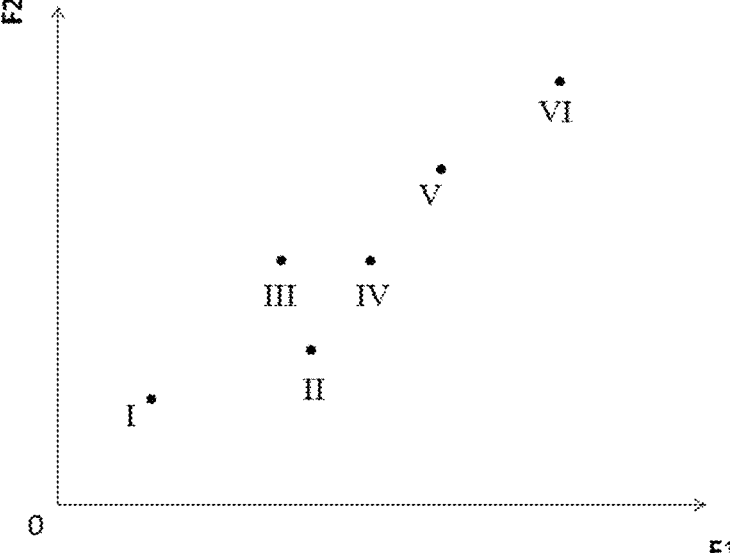
FIG. 9 illustrates a diagram showing a development of values for the factors of a VL-VH pair along a selection method, according to some embodiments.

FIG. 9 shows schematically the development of the values for the factors of a $V_L$-$V_H$ pair along the selection method. The selection method comprises six selection cycles (I, II, II, IV, V, VI) which directly follow one another. The selection method thus starts with selection cycle I and ends with selection cycle VI. For the observed $V_L$-$V_H$ pair, the feature vectors were generated for each pool at the end of a selection cycle and the factors were generated on the basis of the feature vectors. FIG. 9 shows the variables of the factors F1 and F2 for the individual pools.

Figure 10:
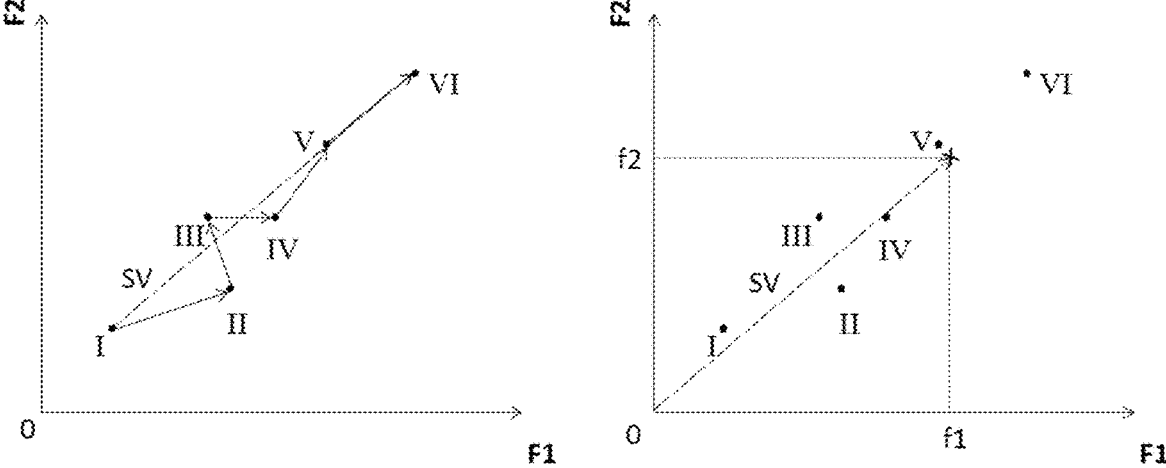
FIG. 10 illustrates diagrams showing a generation of a score value for a VL-VH pair, according to some embodiments.

FIG. 10 shows schematically the generation of a score value for a $V_L$-$V_H$ pair. The same data as in FIG. 9 are shown. Since the selection method proceeded along the selection cycles I→II→III→IV→V→VI, corresponding vectors have been drawn into the coordinate system of the factors F1 and F2. The sum of the vectors yields the dashed sum vector SV. The length of the sum vector SV can, for example, be calculated as a possible score value for the $V_L$-$V_H$ pair. Similarly, it is conceivable that the product f1·f2 of the coordinates (f, f2) of that point which is specified by the sum vector SV is calculated as the score value, if the start of the vector is placed into the origin of the coordinate system. It is conceivable that the summands in the sum vector are weighted before their addition. By means of such weighting, it is, for example, possible for selection cycles leading to a higher enrichment of the antibodies and/or antibody fragments to be weighted higher than selection cycles leading to a lower enrichment.

The score value serves for the quantification of the movement of the variables of the factors from the origin of the coordinate system in the direction of higher values for one or more factors along the selection hierarchy. For example, the described (weighted) sum vector quantifies the movement of points I to VI in the direction of higher values for F1 and F2. Other score values which quantify such a movement are conceivable.

Figure 11:
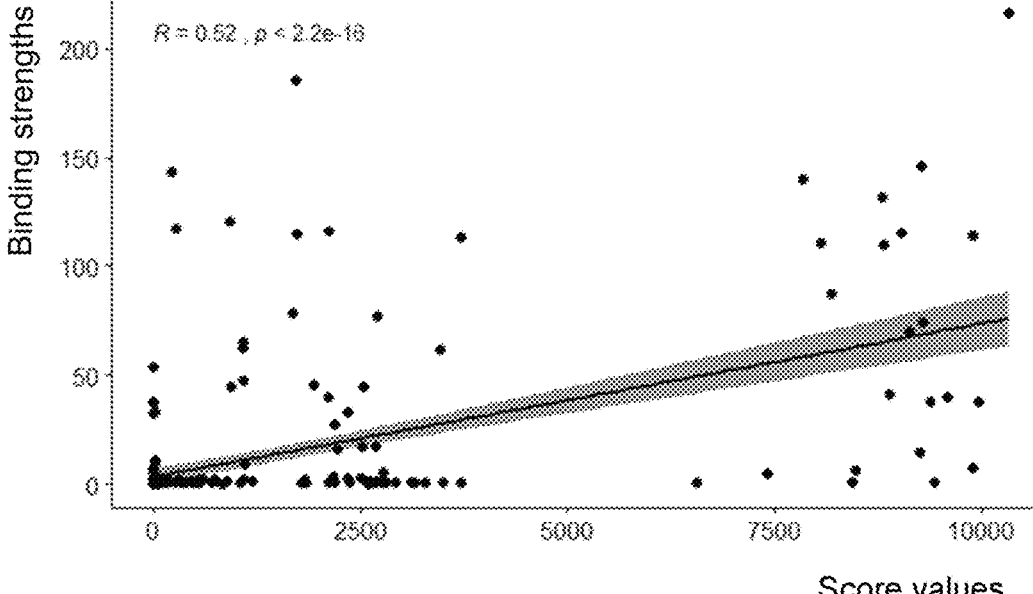
FIG. 11 illustrates a comparison of score values for VL-VH pairs with the binding strengths of the corresponding antibodies/antibody fragments that were determined in an enzyme-linked immunosorbent assay (ELISA), according to some embodiments.

FIG. 11 shows, by way of example, the comparison of the score values for $V_L$-$V_H$ pairs with the binding strengths of the corresponding antibodies/antibody fragments that were determined in an enzyme-linked immunosorbent assay (ELISA). The binding strengths are plotted on the y-axis and the score values are plotted on the x-axis. The values correlate positively with one another.

Figure 12:
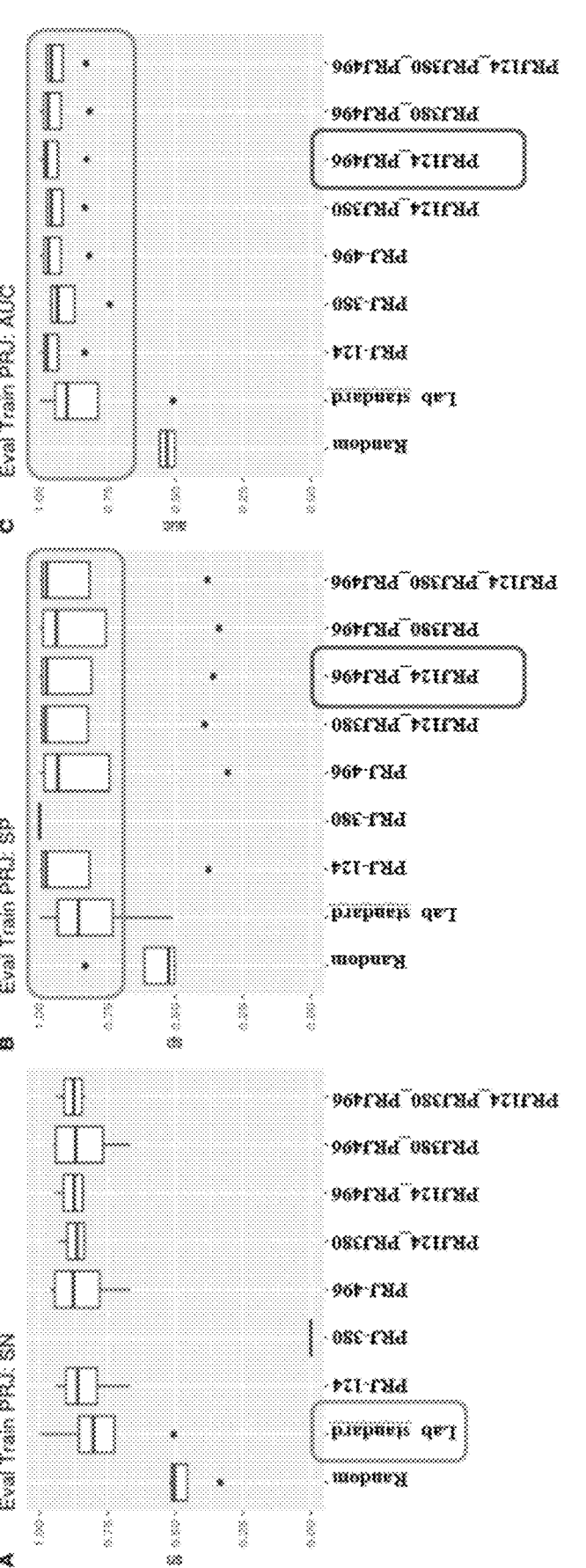
FIG. 12 illustrates a comparison between identifying promising antibodies using a method according to the invention and using a customary procedure, according to some embodiments.

FIG. 12 shows a comparison between identifying promising antibodies using the method according to the invention and using the customary procedure (selection on the basis of the counts of the VH genes (on the basis of the $V_H$ CDR3 counts)). In FIG. 12, three performance values are depicted graphically; A: sensitivity (SN), B: specificity (SP), C: so-called area under receiver operator characteristic curve (AUC). The closer the values to the value of 1, the better the prediction.

The entry "Random" displays a random antibody selection. Here, the values are naturally 0.5.

The entry "Lab standard" shows the result as per a customary procedure (selection of candidates solely on the basis of the $V_H$ CDR3 counts).

The remaining entries display the results of the prediction of promising candidates as per the present invention for various feature vectors. All the predictions are better than customary method.

Identification of $V_L$-$V_H$ Pairs

The feature vectors which are generated when carrying out the present invention are generated for pairs of $V_L$ genes and $V_H$ genes in a pool. In this connection, the $V_L$ gene and the $V_H$ gene of a pair encode the variable domains of light and heavy chains that belong to the same antibody and/or antibody fragment. These pairs are also referred to as $V_L$-$V_H$ pairs in this description. An example as to how these pairs can be identified is described below.

The starting point is a selection method which was carried out for a library of antibodies/antibody fragments. The library of antibodies and/or antibody fragments was introduced to a selection method in order to select antibodies and/or antibody fragments on the basis of their phenotypic properties. The selection method can, for example, be a biopanning method. The selection method comprises at least two successive selection cycles, a first selection cycle and a second selection cycle. Following a selection cycle, genes of the selected antibodies and/or antibody fragments are usually sequenced. The goal of sequencing is to ascertain $V_L$ genes encoding the variable domains of light chains of the antibodies and/or antibody fragments and $V_H$ genes encoding the variable domains of the heavy chains of the antibodies and/or antibody fragments.

In a further step of the method according to the invention, features relating to the $V_L$ and $V_H$ genes are acquired/ascertained. In a following step, the acquired features go into the generation of feature vectors.

The following features can be incorporated in the feature vector for a pair of a $V_L$ gene and a $V_H$ gene:

information about the observed $V_H$ gene (e.g. an unambiguous identifier)

information about the observed $V_L$ gene (e.g. an unambiguous identifier)

the absolute number VH (count) of the observed $V_H$ gene in the pool from the second selection cycle the absolute number VL (count) of the observed $V_L$ gene in the pool from the second selection cycle the absolute number numVH (count) of different $V_H$ genes in the pool from the second selection cycle the absolute number numVL (count) of different $V_L$ genes in the pool from the second selection cycle the absolute number maxVH (count) of that $V_H$ gene which is present in the pool from the second selection cycle with the greatest count the absolute number maxVL (count) of that $V_L$ gene which is present in the pool from the second selection cycle with the greatest count the relative count relVH of the $V_H$ gene in the pool from the second selection cycle (based on the number of the $V_H$ gene which occurs in the pool from the second selection cycle with the greatest count): relVH=VH/maxVH the relative count relVL of the $V_L$ gene in the pool from the second selection cycle (based on the number of the $V_L$ gene which occurs in the pool from the second selection cycle with the greatest count): relVL=VL/maxVL the difference diff (distance) between the count of the observed $V_H$ gene in the pool from the second selection cycle and the count of the observed $V_L$ gene in the pool from the second selection cycle (as amount): diff=|VH-VL| the relative difference relDiff (relative distance) between the count of the $V_H$ gene in the pool from the second selection cycle and the count of the $V_L$ gene in the pool from the second selection cycle (in relation to the count of that gene in the pool from the second selection cycle which occurs with a greater count): relDiff=|VH-VL|/max(VH, VL), where max(VH, VL)=VH for VH>VL and max(VH, VL)=VL for VL≥VH the number prevnum of selection cycles (levels) which were passed through before the second selection cycle the absolute number prevVH of the $V_H$ gene in the pool from the first selection cycle the absolute number prevVL of the $V_L$ gene in the pool from the first selection cycle the difference prevDiff (distance) between the count of the $V_H$ gene from the pool of the first selection cycle and the count of the $V_L$ gene from the pool of the first selection cycle (as amount): prevDiff=|prevVH-prevVL| the relative change in the number of $V_H$ genes from the first selection cycle to the second selection cycle: prevRelDiffV$_H$=(|VH-prevVH|)/max(VH, prevVH), where max(VH, prevVH)=VH for VH>prevVH and max(VH, prevVH)=prevVH for prevVH≥VH the relative change in the number of $V_L$ genes from the first selection cycle to the second selection cycle: prevRelDiffV$_L$=(|VL-prevVL|)/max(VL, prevVL), where max(VL, prevVL)=VL for VL>prevVL and max (VL, prevVL)=prevVL for prevVL≥VL It is conceivable that further items of information besides the stated features go into the generation of feature vectors.

The feature vectors are introduced to a model. The model calculates for each feature vector which is introduced thereto whether the pair of a $V_L$ gene and a $V_H$ gene to which the feature vector is assigned encode variable domains of the light and heavy chains that belong to the same antibody and/or antibody fragment or do not belong to the same antibody and/or antibody fragment.

The model can, for example, be a classification model. Such a classification model assigns each pair of $V_L$ and $V_H$ genes on the basis of its feature vector to one of at least two classes. A first class encompasses those pairs encoding variable domains of the light and heavy chains that belong to the same antibody and/or to the same antibody fragment. A second class encompasses those pairs encoding variable domains of the light and heavy chains that do not belong to the same antibody and/or do not belong to the same antibody fragment.

Expressed simply, the classification model provides information about whether a $V_L$ gene and a $V_H$ gene belong together or not. They belong together when the $V_L$ gene encodes the variable domain of a light chain of an antibody and/or antibody fragment and the $V_H$ gene encodes the variable domain of a heavy chain of the same antibody and/or the same antibody fragment. In such a case, the pair of $V_L$ and $V_H$ genes is also referred to as a $V_L$-$V_H$ pair. They do not belong together when the $V_L$ gene encodes the variable domain of a light chain of an antibody and/or antibody fragment and the $V_H$ gene encodes the variable domain of a heavy chain of a different antibody and/or a different antibody fragment.

The model can also be a regression model. The regression model can, for example, calculate for each pair of a $V_L$ gene and a $V_H$ gene on the basis of its feature vector the probability that the pair of the $V_L$ gene and the $V_H$ gene encode variable domains of light and heavy chains that belong to the same antibody and/or to the same antibody fragment. The result of the calculation of the regression model can, for example, be 0 when it is ruled out that the pair of the $V_L$ gene and the $V_H$ gene encode variable domains of light and heavy chains that belong to the same antibody and/or to the same antibody fragment; the result can, for example, be 1 or 100% when it is certain that the pair of the $V_L$ gene and the $V_H$ gene encode variable domains of light and heavy chains that belong to the same antibody and/or to the same antibody fragment. For the majority of pairs of a $V_L$ gene and a $V_H$ gene, the probability calculated will be between 0 and 1 or 0 and 100%.

The model (e.g. a classification model or a regression model) is preferably created on the basis of a self-learning algorithm. Particularly preferably, the model is created by means of supervised learning.

The model can, for example, be created using known antibodies and/or antibody fragments or using pairs of $V_L$ and $V_H$ genes for which it is known whether they belong together or not. A model can be trained with these data (training data set).

For the creation of classification models, there is a multiplicity of methods, such as, for example, random forest or gradient boosting. For the creation of a regression model, there is likewise a multiplicity of methods, such as, for example, logistic regression. These and further methods for classification and regression are variously described in the prior art (see, for example, Norman Matloff: *Statistical Regression and Classification—From Linear Models to Machine Learning*, Texts in Statistical Science, CRC Press 2017, ISBN 978-1-4987-1091-6; Pratap Dangeti, *Statistics for Machine Learning*, Packt Publishing 2017, ISBN 978-1-78829-575-8).

The result of model creation is a model (e.g. a classification model or a regression model) which is also applicable to $V_L$ and $V_H$ counts of unknown antibodies and/or antibody fragments. The higher the accuracy of the model, the more similar the training data set and the test data set. For example, the accuracy is higher when the same substrates (antigens) are used for training and the test and lower when different substrates are used.

Thus, for any pair of $V_L$ and $V_H$ genes, it can be stated, on the basis of the model, whether they belong together or not (with a defined probability). This information can be outputted in a next step. The output can, for example, be achieved on a screen of a computer system. The information can also be printed out via a printer or stored in a data memory.

The invention claimed is:

1. A method for selecting antibodies or antibody fragments of interest from pools originating from a selection method comprising multiple selection cycles, the method comprising:

conducting the selection method comprising multiple selection cycles to produce one or more pools containing antibodies or antibody fragments, wherein specifically binding antibodies or antibody fragments are enriched;

determining $V_L$ genes encoding the variable domains of light chains of the antibodies or antibody fragments and $V_H$ genes encoding the variable domains of the heavy chains of the antibodies or antibody fragments and their counts in the respective pools;

transmitting features relating to the $V_L$ genes and the $V_H$ genes to a computer system;

forming, using the computer system, feature vectors for pairs of $V_L$ genes and $V_H$ genes in the pools, wherein the $V_L$ gene and the $V_H$ gene of each pair encode variable domains belonging to the same antibody or antibody fragment, and wherein each feature vector for a particular pool comprises the following features:

a count of the $V_L$ gene in the particular pool, a count of the $V_H$ gene in the particular pool, a count of the $V_L$ gene in the preceding pool, a count of the $V_H$ gene in the preceding pool, the absolute difference between the count of the $V_H$ gene in the particular pool and the count of the $V_L$ gene in the particular pool, and the absolute difference between the count of the $V_H$ gene in the preceding pool and the count of the $V_L$ gene in the preceding pool;

identifying, using the computer system, enrichment patterns in the feature vectors of the pools using a multivariate analysis method;

determining, using the computer system, score values for pairs of $V_L$ genes and $V_H$ genes based on the enrichment patterns, wherein the score value for each $V_H$-$V_L$ pair correlates with a respective enrichment of the antibody or antibody fragment with the particular $V_L$ gene and $V_H$ gene in the selection method;

outputting, from the computer system to a user, using a computer monitor, the determined score values;

selecting antibodies or antibody fragments of interest by identifying a largest score value of the determined score values; and using the selected antibody or antibody fragments of interest for therapeutic, immunological, and/or diagnostic purposes.

2. The method of claim 1, wherein the multivariate analysis method comprises:

performing a dimension reduction of all feature vectors of pairs of $V_L$ genes and $V_H$ genes in at least three successive pools, and determining factors for the pairs of $V_L$ genes and $V_H$ genes in the respective pools based on the performed dimension reduction; and wherein the method further comprises:

determining the score values for the pairs of $V_L$ genes and $V_H$ genes by quantifying a change in coordinate values of the factors along successive pools.

3. The method of claim 1, wherein the multivariate analysis method comprises:

determining factors for the pairs of $V_L$ genes and $V_H$ genes in a pool on the basis of the feature vectors, the factors describing the properties of the pairs in a pool with a lower number of variables than the feature vectors; and wherein the method further comprises:

determining the score values for pairs of $V_L$ genes and $V_H$ genes on the basis of the determined factors.

4. The method of claim 1, wherein the multivariate analysis method comprises:

performing a principal component analysis and determining the principal components for pairs of $V_L$ genes and $V_H$ genes in a pool based on the respective feature vectors, and for each pair of a $V_L$ gene and a $V_H$ gene: determining a vector between a start point and an end point in the vector space formed by the principal component analysis, the start point representing the principal components of a pair for a first pool of the selection method and the end point representing the principal components of the same pair for a last pool of the selection method; and wherein the method comprises:

calculating the length of the vector, or calculating the length of a projection of the vector onto an axis of the vector space, or shifting the start point of the vector to the zero point of the vector space and calculating the product of the principal components of the end point of the vector, and using the result of the respective calculation as a score value for a pair of a $V_L$ gene and $V_H$ gene.

5. The method of claim 4, wherein calculating the product of the principal components comprises calculating the product of weighted principal components.

6. The method of claim 1, wherein the multivariate analysis comprises:

performing a principal component analysis and determining the principal components for pairs of $V_L$ genes and $V_H$ genes in a pool on the basis of the respective feature vectors;

and wherein the method comprises:

adding the coordinates of the principal components for each pair of a $V_L$ gene and a $V_H$ gene starting with a first pool of the selection method and ending with a last pool of the selection method; and calculating the length of a vector resulting from adding the coordinates of the principal components, and wherein a score value for a pair of a $V_L$ gene and $V_H$ gene comprises the length of the vector.

7. The method of claim 1, wherein each feature vector comprises one or more features selected from the following list:

the absolute number (count) of different $V_H$ genes in the observed pool: num VH;

the absolute number (count) of different $V_L$ genes in the observed pool: num VL the absolute number (count) of that $V_H$ gene which is present in the observed pool with the greatest count: max VH;

the absolute number (count) of that $V_L$ gene which is present in the observed pool with the greatest count: max VL;

the relative count of the $V_H$ gene in the observed pool (based on the number of the $V_H$ gene which occurs in the observed pool with the greatest count): relVH=VH/max VH;

the relative count of the $V_L$ gene in the observed pool (based on the number of the $V_L$ gene which occurs in the observed pool with the greatest count): relVL=VL/max VL;

the relative difference (relative distance) between the count of the $V_H$ gene in the observed pool and the count of the $V_L$ gene in the observed pool (in relation to the count of that gene in the observed pool which occurs with a greater count): reldiff=|VH−VL|/max (VH, VL), where max (VH, VL)=VH for VH>VL and max (VH, VL)=VL for VL≥VH;

the number of selection cycles (levels) which were passed through before the observed selection cycle: prevnum;

normalized count of the $V_H$ genes in the observed pool: rpm VH=(VH/sum VH)*1000000, where sumVH is the sum of the counts VH of all $V_H$ genes in the observed pool;

normalized count of the $V_L$ genes in the observed pool: rpmVL=(VL/sumVL)*1000000, where sum VL is the sum of the counts VL of all $V_L$ genes in the observed pool;

normalized count of the $V_H$ genes in the preceding pool: prevRpmVH=(prevVH/prevSumVH)*1000000, where prevSumVH is the sum of the counts $V_H$ of all $V_H$ genes in the preceding pool;

normalized count of the $V_L$ genes in the preceding pool: prevRpmVL=(prevVL/prevSumVL)*1000000, where prevSumVL is the sum of the counts VL of all $V_L$ genes in the preceding pool;

the relative change in the number of $V_H$ genes from the first selection cycle to the second selection cycle: prevRelDiffV$_H$=(|VH−prev VH|)/max (VH, prevVH), where max (VH, prevVH)=VH for VH>prevVH and max (VH, prevVH)=prevVH for prevVH≥VH; or the relative change in the number of $V_L$ genes from the first selection cycle to the second selection cycle: prevRelDiffV$_L$=(|VL−prevVL|)/max (VL, prevVL), where max (VL, prev VL)=VL for VL>prevVL and max (VL, prevVL)=prevVL for prevVL≥$V_L$.

8. The method of claim 1, wherein the feature vectors comprise the following features:

normalized count of the $V_L$ genes in the observed pool: rpm VL=(VL/sum VL)*1000000, where sumVL is the sum of the counts VL of all $V_L$ genes in the observed pool;

normalized count of the $V_H$ genes in the observed pool: rpmVH=(VH/sumVH)*1000000, where sumVH is the sum of the counts VH of all $V_H$ genes in the observed pool;

the absolute difference (diff) between the count of the $V_H$ gene in the particular pool and the count of the $V_L$ gene in the particular pool (diff=|VH−VL|);

the relative difference between the count of the $V_H$ gene in the observed pool and the count of the $V_L$ gene in the observed pool (in relation to the count of that gene in the observed pool which occurs with a greater count): reldiff=|VH−VL|/max (VH, VL), where max (VH, VL)=VH for VH>VL and max (VH, VL)=VL for VL≥VH;

the absolute difference (prevDiff) between the count of the $V_H$ gene in the preceding pool and the count of the $V_L$ gene in the preceding pool (prevDiff=|prevVH−prevVL|);

normalized count of the $V_H$ genes in the preceding pool: prevRpmVH=(prevVH/prevSumVH)*1000000, where prevSumVH is the sum of the counts VH of all $V_H$ genes in the preceding pool;

normalized count of the $V_L$ genes in the preceding pool: prevRpmVL=(prevVL/prevSumVL)*1000000, where prevSumVL is the sum of the counts VL of all $V_L$ genes in the preceding pool;

the number of selection cycles (levels) which were passed through before the observed selection cycle: prevnum;

the logarithm to the base 2 of the ratio of the normalized count of the $V_H$ genes in the observed pool to the normalized count of the $V_H$ genes in the preceding pool: logRpmVH=log 2(rpm VH/prevRpms VH); and the logarithm to the base 2 of the ratio of the normalized count of the $V_L$ genes in the observed pool to the normalized count of the $V_L$ genes in the preceding pool: logRpmVL=log 2(rpm VL/prevRpms VL).

9. The method of claim 1, wherein the scores values comprise a first score value and a second score value calculated for each pair of a $V_L$ gene and a $V_H$ gene, the first score value for the enrichment with respect to a murine target and the second score value for a human target.

10. The method of claim 9, further comprising:

determining a ranking list for the pairs of $V_L$ genes and $V_H$ genes based on the score values, wherein the first score value and the second score value calculated for each pair of a $V_L$ gene and a $V_H$ gene individually has a rank order in the ranking list.

11. The method of claim 1, further comprising determining a ranking list for the pairs of $V_L$ genes and $V_H$ genes based on the score values, wherein outputting the score values comprises outputting the ranking list to the user.

\* \* \* \* \*